(12) United States Patent
Bhoge et al.

(10) Patent No.: US 9,085,592 B2
(45) Date of Patent: Jul. 21, 2015

(54) PROCESS FOR THE PREPARATION OF FOSAMPRENAVIR CALCIUM

(75) Inventors: Satish Manohar Bhoge, Ahmed Nagar (IN); Prakash Kshirsagar, Pune (IN); Santosh Richhariya, Sagar (IN); Kaptan Singh, Ghaziabad (IN)

(73) Assignee: RANBAXY LABORATORIES LIMITED, New Delhi (IN)

( * ) Notice: Subject to any disclaimer, the term of this patent is extended or adjusted under 35 U.S.C. 154(b) by 66 days.

(21) Appl. No.: 13/496,281

(22) PCT Filed: Sep. 16, 2010

(86) PCT No.: PCT/IB2010/054191
§ 371 (c)(1),
(2), (4) Date: May 14, 2012

(87) PCT Pub. No.: WO2011/033469
PCT Pub. Date: Mar. 24, 2011

(65) Prior Publication Data
US 2012/0220786 A1  Aug. 30, 2012

(30) Foreign Application Priority Data
Sep. 16, 2009 (IN) .......................... 1933/DEL/2009

(51) Int. Cl.
*C07F 9/117* (2006.01)
*C07F 9/655* (2006.01)

(52) U.S. Cl.
CPC ................................. *C07F 9/65515* (2013.01)

(58) Field of Classification Search
USPC ........................................................ 549/222
See application file for complete search history.

(56) References Cited

U.S. PATENT DOCUMENTS

| 6,436,989 B1 | 8/2002 | Hale et al. ..................... 514/473 |
| 6,514,953 B1 * | 2/2003 | Armitage et al. ............... 514/99 |
| 6,559,137 B1 * | 5/2003 | Tung et al. ..................... 514/99 |

FOREIGN PATENT DOCUMENTS

| WO | WO 00/04033 | 1/2000 | ............. C07F 9/655 |
| WO | WO 01/00635 A2 | 6/2000 | ................ C07F 9/00 |
| WO | WO 01/00635 A2 * | 1/2001 | ................ C07F 9/00 |

OTHER PUBLICATIONS

The Catalyst Technical Handbook, 2008 Johnson Matthey Plc, p. 10, section 2.1.7 and p. 31 table.*
Armarego, W.L.F., Purification of Laboratory Chemicals, Fifth Edition, Butterworth Heinemann, 2003, Chapter 1, p. 1-30.*
Furfine et al., "Preclinical Pharmacology and Pharmacokinetics of GW433908, a Water-Soluble Prodrug of the Human Immunodeficiency Virus Protease Inhibitor Amprenavir", *Antimicrobial Agents and Chemotherapy*, 48(3):791-798 (2004).

* cited by examiner

*Primary Examiner* — Noble Jarrell
*Assistant Examiner* — John Mauro

(57) ABSTRACT

The present invention relates to process for the preparation of fosamprenavir calcium.

9 Claims, No Drawings

PROCESS FOR THE PREPARATION OF FOSAMPRENAVIR CALCIUM

FIELD OF THE INVENTION

The present invention relates to process for the preparation of fosamprenavir calcium.

BACKGROUND OF THE INVENTION

Fosamprenavir calcium is chemically the calcium salt of (3S)-tetrahydrofuran-3-yl-(1S,2R)-3-[[(4-aminophenyl)sulfonyl](isobutyl)amino]-1-benzyl-2-(phosphono oxy)propyl carbamate of Formula I:

FORMULA I

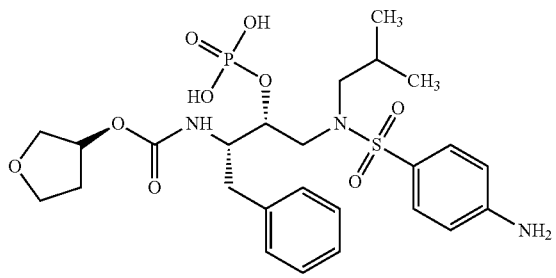

Fosamprenavir calcium is a prodrug of amprenavir, an inhibitor of HIV protease, and is indicated in combination with other antiretroviral agents for the treatment of human immunodeficiency virus (HIV-1) infection.

U.S. Pat. No. 6,436,989 provides a process for the preparation of sodium salt of fosamprenavir which involves treating fosamprenavir with aqueous sodium bicarbonate, isolating the sodium salt of fosamprenavir by a resin column and lyophilization.

U.S. Pat. No. 6,514,953 provides processes for the preparation of fosamprenavir which includes hydrogenating (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate of Formula II

FORMULA II

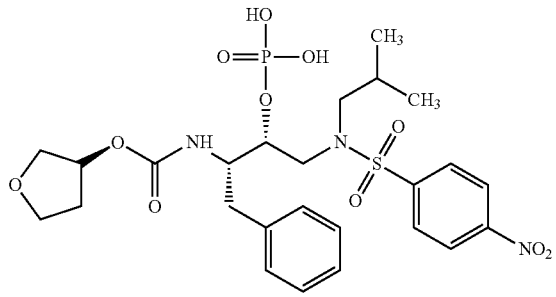

using palladium-carbon in the presence of sodium bicarbonate or sodium hydroxide, water and industrial methylated spirit. After hydrogenation, the reaction mixture is filtered to remove the catalyst and the filtrate is treated with aqueous solution of calcium acetate to obtain fosamprenavir calcium.

SUMMARY OF THE INVENTION

The present inventors have developed a process for the direct preparation of fosamprenavir calcium from the calcium salt of the compound of Formula II through reduction. The present process avoids the additional step of first obtaining fosamprenavir or its sodium salt and then converting it to fosamprenavir calcium. Thus the present invention provides a simple, more industrially-efficient, and economic process for the preparation of fosamprenavir calcium.

DETAILED DESCRIPTION OF THE INVENTION

A first aspect of the present invention provides a process for the preparation of a calcium salt of (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate of Formula II, wherein the process comprises:

a) treating (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate of Formula II or a salt of (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate of Formula II, with the proviso that the salt is not a calcium salt, with a source of calcium ions, to obtain a calcium salt of (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate of Formula II,

FORMULA II

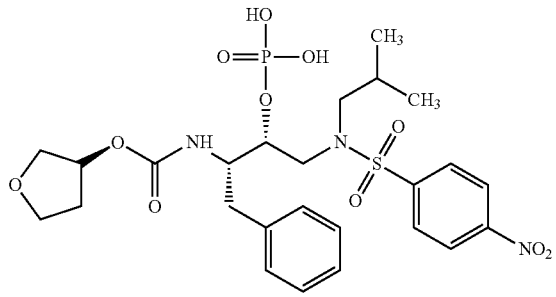

wherein the salt referred to above is preferably selected from the group consisting of lithium, sodium, potassium, magnesium, and ammonium (including alkyl ammonium).

and b) optionally isolating the calcium salt of (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate of Formula II from the reaction mixture thereof.

A second aspect of the present invention provides a process for the preparation of fosamprenavir calcium, wherein the process comprises, a) reducing a calcium salt of (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate of Formula II, and

FORMULA II

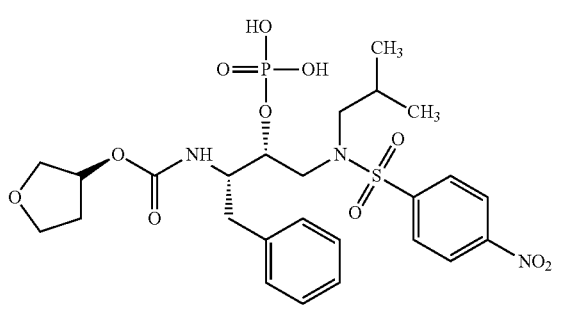

b) isolating fosamprenavir calcium from the reaction mixture thereof.

A third aspect of the present invention provides a process for the preparation of fosamprenavir calcium, wherein the process comprises, a) treating (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate of Formula II or a salt of (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate of Formula II, with the proviso that the salt is not a calcium salt, with a source of calcium ions, to obtain a calcium salt of (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate of Formula II,

FORMULA II

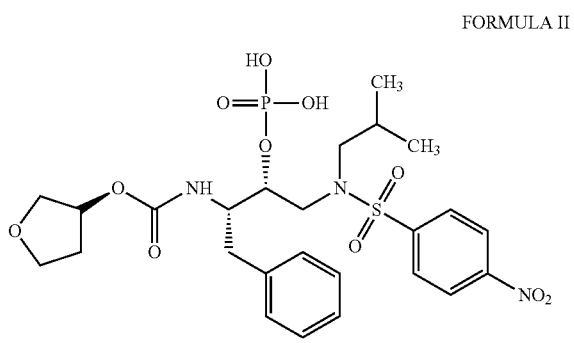

wherein the salt referred to above is preferably selected from the group consisting of lithium, sodium, potassium, magnesium, and ammonium (including alkyl ammonium).

b) reducing the calcium salt of (3S)-tetrahydrofuran-3-yl [(2S,3R)-4-{(2-methylpropyl)[(4-nitrophenyl)sulfonyl]amino}-1-phenyl-3-(phosphonooxy)butan-2-yl] carbamate of Formula II, and c) isolating fosamprenavir calcium from the reaction mixture thereof.

(3S)-Tetrahydrofuran-3-yl[(2S,3R)-4-{(2-methylpropyl) [(4-nitrophenyl)sulfonyl]amino}-1-phenyl-3-(phosphonooxy)butan-2-yl]carbamate of Formula II may be prepared according to the methods provided in U.S. Pat. Nos. 6,514, 953 or 6,436,989. The starting compound of Formula II may also be in the form a salt, with a proviso that the salt is not a calcium salt, wherein the salt is preferably selected from the group consisting of lithium, sodium, potassium, magnesium, and ammonium (including alkyl ammonium). The salt of the compound of Formula II, wherein the salt is preferably selected from the group consisting of lithium, sodium, potassium, magnesium, and ammonium (including alkyl ammonium), may be prepared by contacting the compound of Formula II with a source of monovalent or divalent cations. For example, the starting compound of Formula II may be a sodium or potassium salt. The compound of Formula II or its salt, wherein the salt is preferably selected from the group consisting of lithium, sodium, potassium, magnesium, and ammonium (including alkyl ammonium), may also be used as obtained directly from a reaction mixture, in which compound of Formula II or its salt is formed, without isolation.

The compound of Formula II or a salt of the compound of Formula II, with the proviso that the salt is not a calcium salt, is treated with a source of calcium ions, to obtain the calcium salt of the compound of Formula II, wherein the salt is preferably selected from the group consisting of lithium, sodium, potassium, magnesium, and ammonium (including alkyl ammonium).

The treatment with a source of calcium ions may be carried out in the presence of a solvent system comprising an organic solvent, water or a mixture thereof. The organic solvent may be a water-miscible organic solvent, for example, a $C_{1-3}$ alkanol. The solvent system may be, for example, a mixture of water and denaturated or industrial methylated spirit. The source of calcium ions may be, for example, calcium acetate, calcium chloride or calcium hydroxide. The source of calcium ions may be in the form of aqueous solution. The treatment with a source of calcium ions may be carried out at a temperature of about 15° C. to about 80° C., for example about 35° C. to about 60° C. The formation of the calcium salt of the compound of Formula II may be facilitated by stiffing the reaction mixture for about 10 minutes to about 10 hours. The calcium salt of the compound of Formula II may be optionally isolated from the reaction mixture or directly used in the subsequent step without isolation. The isolation of the calcium salt of the compound of Formula II may be carried out by filtration, decantation, solvent precipitation, evaporation, centrifugation, distillation or a combination thereof.

The calcium salt of the compound of Formula II is reduced to obtain fosamprenavir calcium. The reduction may be carried out using a reducing agent or a hydrogenation catalyst, for example, formic acid or hydrogen with palladium or palladium-carbon. The reduction may be carried out in the presence of a solvent. The solvent may be, for example, $C_{1-3}$ alkanol, ethyl acetate, water, acetone, denaturated or industrial methylated spirit or a mixture thereof. The reduction may be carried out at a temperature of about 10° C. to about 80° C., for example about 15° C. to about 35° C. Fosamprenavir calcium may be isolated from the reaction mixture by filtration, decantation, solvent precipitation, evaporation, centrifugation, distillation or a combination thereof. A further optional purification may be carried out by treating with a water-miscible organic solvent or water or a mixture thereof. For example, the fosamprenavir calcium may be purified by dissolving in a solvent, filtering and precipitating with an antisolvent.

A third aspect of the present invention provides a calcium salt of the compound of Formula II.

FORMULA II

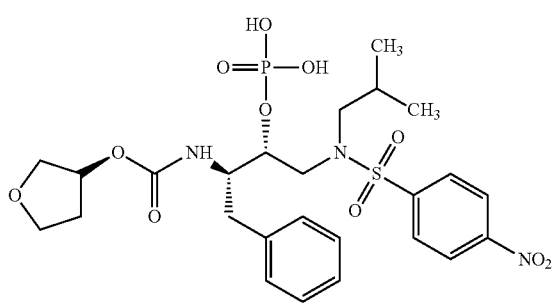

A fourth aspect of the present invention provides the use of a calcium salt of the compound of Formula II for the preparation of fosamprenavir calcium.

While the present invention has been described in terms of its specific embodiments, certain modifications and equivalents will be apparent to those skilled in the art and are intended to be included within the scope of the present invention.

EXAMPLES

Example 1

Preparation of Calcium Salt of (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate (Formula II)

(3S)-Tetrahydro-3-furanyl(1S,2R)-3-[[(4-nitrophenyl)-sulfonyl](isobutyl)amino]-1-benzyl-2-(hydroxy) propyl carbamate (25 g) was stirred for 10 minutes at 20° C. to 25° C. with pyridine (32.75 g). Methyl isobutyl ketone (125 mL) was added to the reaction mixture at 20° C. to 25° C. Phosphorus oxychloride (16.28 g) was slowly added to the reaction mixture at 20° C. to 30° C. in 30 minutes. The reaction mixture was stirred for 2.5 hours at 25° C. to 30° C. 2N Hydrochloric acid (81 mL) was slowly added into the reaction mixture at 20° C. to 30° C. The reaction mixture was heated at 65° C. to 70° C. and stirred for 3 hours. The reaction mixture was cooled to 20° C. to 25° C. and stirred for 10 to 15 minutes. The layers were separated and the aqueous layer was extracted with methyl isobutyl ketone (47 mL). Two methyl isobutyl ketone layers were combined and washed with de-ionized water (2×94 mL). Methyl isobutyl ketone (125 mL) was recovered at 50° C. under reduced pressure to obtain a concentrated mixture. Methyl isobutyl ketone (50 mL) was added to the mixture to obtain a solution. De-ionized water (100 mL) was added to the solution followed by slow addition of 30% w/v sodium hydroxide (10 g) solution at 20° C. to 30° C. The reaction mixture was stirred at 20° C. to 25° C. for 30 minutes and the layers were separated. The aqueous layer was washed with methyl isobutyl ketone (3×25 mL) at 20° C. to 25° C. The aqueous layer was subsequently washed with ethyl acetate (2×25 mL). Denatured spirit (92 mL) was added to the aqueous layer at 20° C. to 25° C. The reaction mixture was heated at 40° C. to 50° C. and a solution of calcium acetate (6.41 g in 91 mL of de-ionized water) was added at 40° C. to 50° C. The resultant mixture was stirred at 40° C. to 50° C. for 30 minutes. The reaction mixture was cooled to 20° C. to 25° C. and stirred for further 2 hours. The solid was filtered, washed with water and dried at 40° C. under vacuum to obtain the title compound.

Yield: 20.52 g

Example 2

Preparation of Fosamprenavir Calcium

Calcium salt of (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate (5 g) was added into a mixture of methanol (50 mL) and ethyl acetate (50 mL) at 20° C. to 25° C. and stirred for 20 minutes. The reaction mixture was filtered through Celite bed and the bed was washed with methanol:ethyl acetate (1:1, 12.5 mL). Palladium-carbon (10%; 1 g) was added to the filtrate and stirred at 20° C. to 25° C. under hydrogen pressure 30 to 40 psi for 4 to 5 hours. The resultant mixture was filtered over Celite bed and the bed was washed with methanol:ethylacetate (1:1; 12.5 mL). The solvent was removed from the filtrate under vacuum at 40° C. to 45° C. to obtain a residue. De-ionized water (50 mL) was added to the residue and stirred at 90° C. to 95° C. for 2 to 3 hours. The reaction mixture was cooled to 20° C. to 25° C. and stirred for 2 hours further. The solid obtained was filtered, washed with de-ionized water (10 mL) and dried at 40° C. Industrial methylated spirit (52.5 mL) was added to the dried solid at 20° C. to 25° C., heated at 70° C. to 72° C., stirred for 15 minutes, filtered at hot condition through Celite bed and washed with hot industrial methylated spirit (17.5 mL). The filtrate was heated at 70° C. to 72° C. followed by the addition of de-ionized water (10.5 mL). The mixture was cooled to 20° C. to 25° C., stirred for 2 hours further, filtered, washed industrial methylated spirit: de-ionized water (1:1, 10 mL) and dried at 40° C. under vacuum to obtain the title compound.

Yield: 1.7 g

We claim:
1. A process for the preparation of fosamprenavir calcium, wherein the process comprises
a) treating (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate of Formula II

FORMULA II

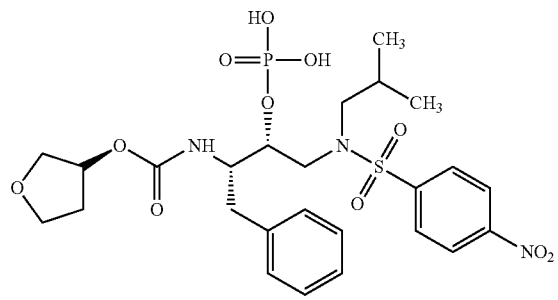

or a starting salt of (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate of Formula II, with a source of calcium ions, to obtain a calcium salt of the compound (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate of Formula II, wherein the starting salt is selected from lithium, sodium, potassium, magnesium, and ammonium;
b) isolating the solid calcium salt of the compound (3S)-tetrahydrofuran-3-yl[(2S,3R)-4-{(2-methylpropyl)[(4- nitrophenyl)sulfonyl]amino}-1-phenyl-3-(phosphonooxy)butan-2-yl]carbamate of Formula II from the reaction mixture thereof;

c) reducing the nitro group of the calcium salt of the compound (3S)-tetrahydrofuran-3-yl[(2S,3R)-4-{(2-methylpropyl)[(4-nitrophenyl)sulfonyl]amino}-1-phenyl-3-(phosphonooxy)butan-2-yl]carbamate of Formula II to an amino group; and d) isolating fosamprenavir calcium from the reaction mixture thereof.

2. The process according to claim 1, wherein the reduction is carried out using a reducing agent which does not use hydrogen gas or which uses hydrogen gas and a hydrogenation catalyst.

3. The process according to claim 1, wherein the reduction is carried out in the presence of a solvent.

4. The process according to claim 3, wherein the solvent is $C_{1-3}$ alkanol, ethyl acetate, water, acetone, denaturated or industrial methylated spirit or a mixture thereof.

5. The process according to claim 1, wherein step a) is carried out in the presence of a solvent system comprising an organic solvent, water or a mixture thereof.

6. The process according to claim 5, wherein the organic solvent is a water miscible organic solvent.

7. The process according to claim 6, wherein the water miscible organic solvent is a $C_{1-3}$ alkanol.

8. The process according to claim 1, wherein the source of calcium ions is calcium acetate, calcium chloride or calcium hydroxide.

9. The process according to claim 1 wherein the starting salt used in step a) is a sodium or potassium salt.

* * * * *